United States Patent [19]

Falk

[11] Patent Number: 4,570,496
[45] Date of Patent: Feb. 18, 1986

[54] MOLTEN METAL SAMPLER WITH TELLURIUM ADDITIVE

[76] Inventor: Richard A. Falk, 519 Westminster Dr., Waukesha, Wis. 53186

[21] Appl. No.: 538,149

[22] Filed: Oct. 3, 1983

[51] Int. Cl.[4] ......................... G01N 1/10; G01K 13/12
[52] U.S. Cl. .................................. 73/864.58; 75/130; 374/139
[58] Field of Search ................... 374/139, 157, 26, 19; 73/864.58, DIG. 9; 136/234; 75/130

[56] References Cited

U.S. PATENT DOCUMENTS

| | | | |
|---|---|---|---|
| 3,452,602 | 7/1969 | Hackett | 73/864.58 X |
| 3,559,452 | 2/1971 | Perbix et al. | 73/864.58 |
| 3,818,762 | 6/1974 | Kraus et al. | 136/234 |
| 3,844,172 | 10/1974 | Jeric | 374/157 X |
| 3,946,594 | 3/1976 | Surinx | 374/26 |
| 4,059,996 | 11/1977 | Cure | 374/157 X |
| 4,261,740 | 4/1981 | Plessers | 75/129 |
| 4,274,284 | 6/1981 | Hance | 374/26 X |

FOREIGN PATENT DOCUMENTS 2002664 2/1979 United Kingdom ............ 73/864.58

Primary Examiner—Daniel M. Yasich
Attorney, Agent, or Firm—Fuller, House & Hohenfeldt

[57] ABSTRACT

A tellurium insert for a molten metal sampling cup for determining the carbon content of iron is pre-cast or cast insitu and arranged around a centrally located heat sensor tube which positively positions the insert in the sample cup.

8 Claims, 8 Drawing Figures

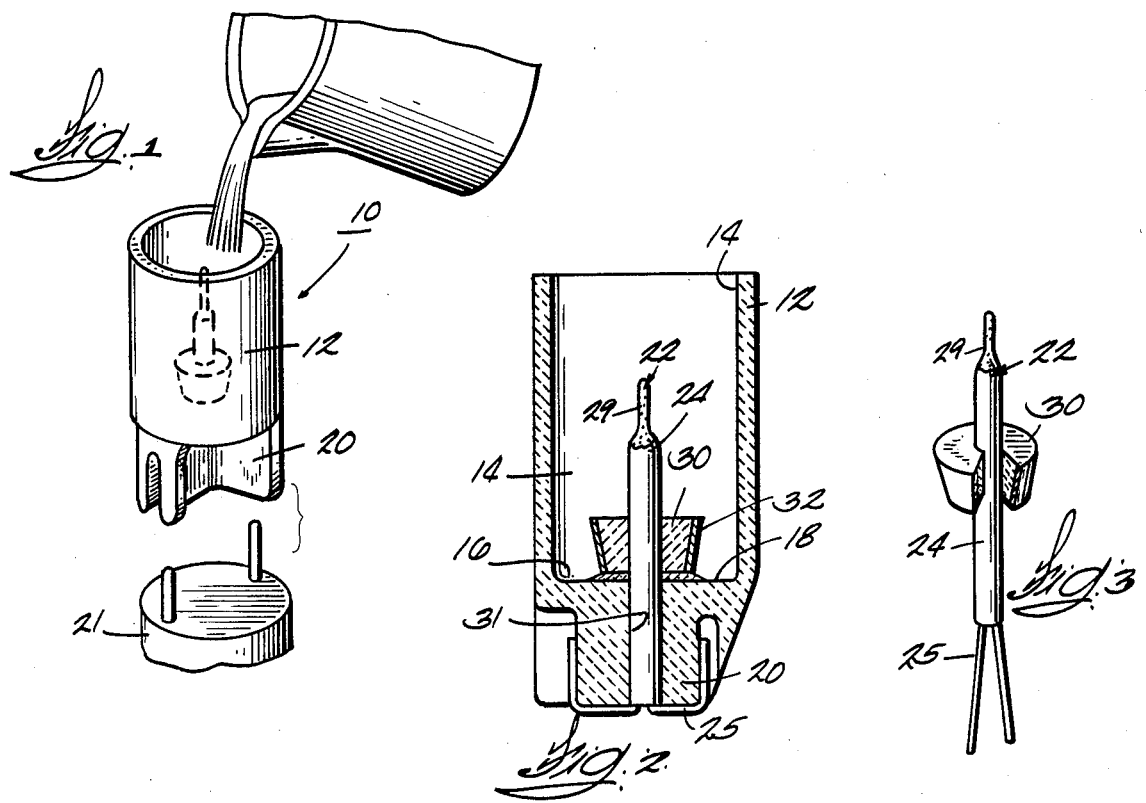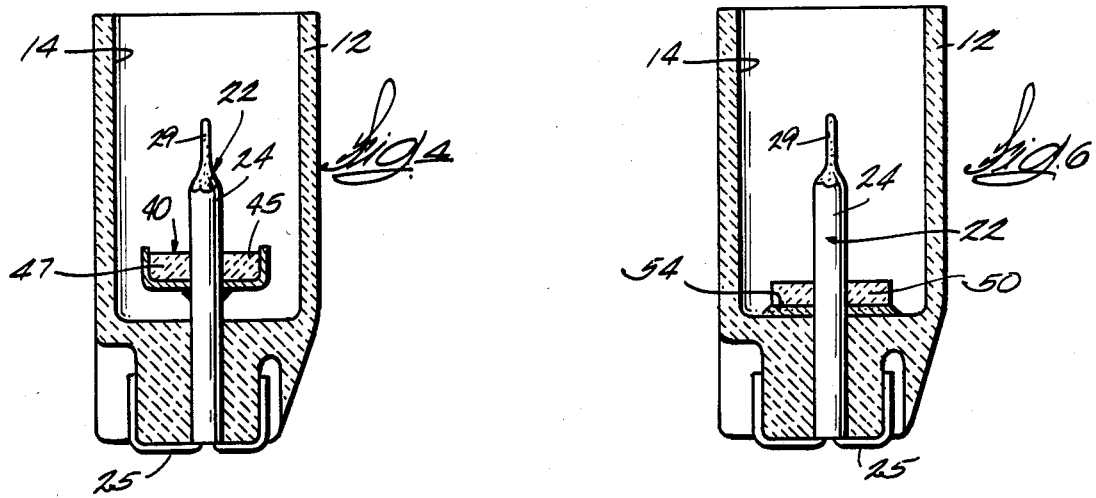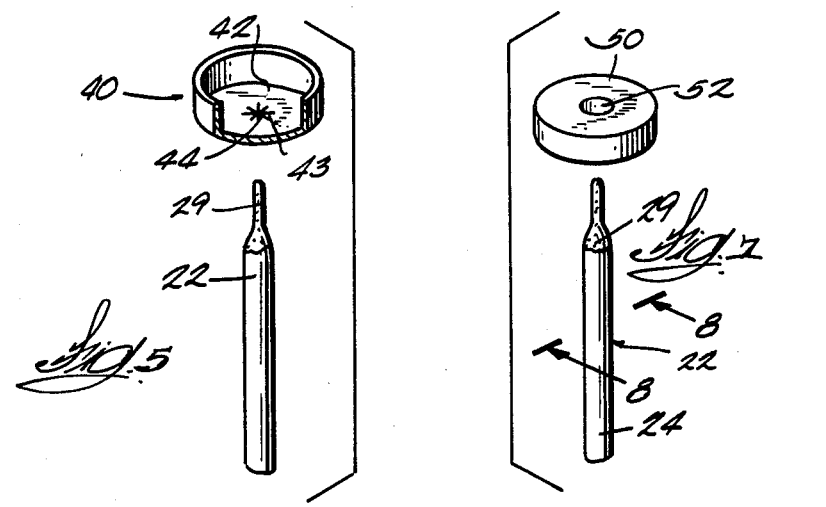

MOLTEN METAL SAMPLER WITH TELLURIUM ADDITIVE

BACKGROUND OF THE INVENTION

The present invention relates to a sampler cup in which a sample of molten iron is treated with tellurium to enable determination of the solidus temperature and the carbon content of the sample. Various prior art patents, such as U.S. Pat. Nos. 4,059,996 and 4,261,740 discuss the placement of quantities of tellurium in sample cups for the purpose of delaying graphite formation so that the cooling curve of a hypereutetic iron sample can be obtained to provide a usable liquidus arrest temperature for carbon determination.

In the prior art, in addition to the use of blobs of material containing tellurium, the prior art also includes use of a wash of tellurium which covers the inside walls of the crucible and bottom of the crucible. These prior art techniques do not involve the use of a standardized amount of tellurium or a consistent location of the tellurium in each sample cup. As a result, non-uniform samples were produced and the test results were not always representative or comparable.

SUMMARY OF THE INVENTION

The present invention provides a tellurium additive or insert for sampling cups which contain a measured amount of tellurium. The insert is positively located or positioned in the cups to provide more uniform and consistent results than the prior art cups. In this regard, washer-shaped or disc-like castings containing tellurium are either pre-molded or molded insitu. These castings have a central aperture which receives the thermocouple projective tube which projects into the cup cavity and is concentric therewith. The tube centers the castings in the cup.

Further objects, advantages and features of the invention will become apparent from the disclosure.

DESCRIPTION OF THE DRAWINGS

FIG. 1 is a perspective view of one embodiment of the tellurium insert of the invention being formed in place;

FIG. 2 is an enlarged sectional view of the sampler cup of FIG. 1;

FIG. 3 is a perspective view of the insert and the heat sensor;

FIG. 4 is a sectional view of a modified embodiment of the invention;

FIG. 5 is a perspective view of the molding dish illustrated in FIG. 4;

FIG. 6 is a sectional view of a modified embodiment of the invention;

FIG. 7 is a perspective view of the tellurium additive shown in FIG. 6; and

FIG. 8 is a sectional view along lines 8—8 of FIG. 7.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows a sampling cup 10 which can be molded from foundry sand and which includes wall means 12 defining a cylindrical cavity 14 for receiving the sample. Wall means 16 also form a floor 18. A connector structure 20 is provided which is connectible to an electrical connector 21 which provides electrical connection to the heat sensor or thermocouple unit 22 contained within a temperature resistant glass or ceramic tube 24. In the disclosed construction, the tube 24 is formed from ceramic material with two spaced insulated wire apertures 25 (FIG. 8). The hot junction of the wires is protected by a coating 29 of ceramic cement. The tube 24 extends into the cavity 14 through an aperture 31. The tube 24 is anchored in the aperture 31 in concentric or centered relationship with respect to wall 12. This results in positively positioning the tellurium casting in the center of the cavity 14, as hereinafter described.

In the construction disclosed in FIGS. 1, 2, and 3, a frusto-conical tellurium casting 30 is molded in place around the tube 24 by pouring a tellurium, sand and binder mix into a frusto-conical mold 32 which is arranged around the tube 24. The mold can be formed of a thin member such as tape 19. Alternatively, the frusto-conical casting can be pre-molded and placed in assembly with the tube 24, and the assembly can then be cemented in place by refractory cement.

FIGS. 4 and 5 show a modified embodiment in which the mold is a dish 40 provided with an aperture 42 having radial slits 43 with flexible segments 44 which can be pushed over the tube 24 to provide a seal and tight fit on the tube 24. The tellurium mix can then be poured in the dish cavity 45 to form the insert 47 (FIG. 4).

FIGS. 6 and 7 show a further modified embodiment in which a pre-cast washer or disc 50 with a pre-formed central aperture 52 is molded from the tellurium sand and binder mix and then inserted around the tube 24 and connected in place by refractory cement 54.

In all embodiments, significant portions of the tellurium casting are located or spaced from the floor 16. This insures exposure of the tellurium to the molten iron. A tellurium coating or blob on the floor or wall of the cup, as in prior art devices, is readily covered by a skin of iron, chilled by the walls or bottom of the cup, and hence the tellurium is not readily and completely vaporized or dispersed throughout the molten metal to provide uniformity in the sample of hypereutetic iron necessary for measurement of carbon content.

With the FIG. 4 embodiment, the tellurium mix is spaced a significant distance off the floor 16. This will insure that the tellurium is not covered over by a metal skin, which can cause transfer of the tellurium vapor through the walls of the mold cavity rather than into the sample. In addition, in all embodiments the tellurium mix is retained in place during gasification. The upwardly tapered wall 32 (FIG. 1) prevents the tellurium from floating out of place.

I claim:

1. A molten metal sampler cup comprising side wall means defining a receptacle for molten metal, wall means defining a base and connector plug, a heat sensing element, a bore through the base for receiving a protective tube for the heat sensing element which projects into said receptacle, and a tellurium insert unit having a measured amount of tellurium formed in an annular shaped form, said unit being arranged around the heat sensor and spaced from at least said side wall means, and means for securing the tellurium insert unit in the interior of said cup.

2. The sampler of claim 1 wherein said tellurium unit has an aperture which receives the protective tube.

3. The sampler of claim 1 in which the tellurium unit is conical-shaped to provide a frusto-conical shaped tellurium body with the large cross-section remote from the floor of the cup.

4. The sampler of claim 1 wherein the tellurium unit includes a dish with a central aperture for receiving the heat sensor tube for positively locating the tellurium insert with respect to the interior of the said cup to provide consistent test results.

5. The sampler of claim 1 in which the tellurium unit is in the form of a disc with a central aperture which receives the heat sensor tube.

6. The sampler of claim 1 wherein said bore in said receptacle is centered with respect to said side wall means and said insert is concentric with respect to said tube and said side wall means.

7. The molten metal sampler cup comprising wall means defining receptacle side walls with a base and an upper wall lip, a heat sensor tube projecting through said base and an annular tellurium unit containing a measured amount of tellurium supported on said tube and spaced from said base and the side walls and intermediate said base and said lip at a pre-selected and secured position and remote from at least said side walls to prevent formation of a metal skin from the molten metal in said sampler cup over said tellurium unit.

8. The combination of a molten metal sampler cup and a tellurium unit of an annular pre-selected shape and containing a measured amount of tellurium and further comprising wall means defining receptacle side walls with a base, a heat sensor tube projecting through said base and through said tellurium unit and said unit positioned by said tube in a secured, centered position and spaced with respect to said receptacle side wall means and spaced from at least said side wall means.

* * * * *